United States Patent [19]

Farooq et al.

[11] 4,338,468
[45] Jul. 6, 1982

[54] α-PROP-1-YNYL-3-PHENOXYBENZYL ALCOHOLS

[75] Inventors: Saleem Farooq, Ettingen; Peter Ackermann, Reinach; Jozef Drabek, Oberwil; Laurenz Gsell, Basel; Odd Kristiansen, Möhlin; Rudolf Wehrli, Rheinfelden, all of Switzerland

[73] Assignee: Ciba-Geigy Corporation, Ardsley, N.Y.

[21] Appl. No.: 216,223

[22] Filed: Dec. 9, 1980

Related U.S. Application Data

[63] Continuation-in-part of Ser. No. 49,390, Jun. 18, 1979, abandoned.

[30] Foreign Application Priority Data

Jun. 27, 1978 [CH] Switzerland .................. 6994/78
Apr. 19, 1979 [CH] Switzerland .................. 3681/79

[51] Int. Cl.³ .................................. C07C 43/263
[52] U.S. Cl. .............................. 568/637; 568/638; 260/465 F; 564/430; 424/341; 424/330; 424/304
[58] Field of Search ................... 568/637, 638

[56] References Cited

U.S. PATENT DOCUMENTS 4,115,456  9/1978  Gante et al. ................ 568/637
4,141,921  2/1979  Karrer ........................ 568/638 X
4,151,294  4/1979  Kurmeier et al. ........... 568/637 X Primary Examiner—Bernard Helfin
Attorney, Agent, or Firm—Frederick H. Rabin

[57] ABSTRACT

α-Prop-1-ynyl-3-phenoxybenzyl alcohols of the formula

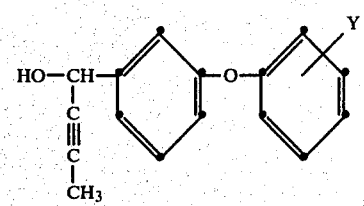

wherein Y represents hydrogen, halogen, $C_1$–$C_4$alkyl, $C_1$–$C_3$alkoxy, cyano or dimethylamino, a process for their manufacture and their use as intermediates for the synthesis of compounds which are suitable for pest control, and which are especially suitable because of their low fish toxicity, for the control of rice pests e.g. *Chilo suppressalis* in rice paddies where fish are kept.

6 Claims, No Drawings

α-PROP-1-YNYL-3-PHENOXYBENZYL ALCOHOLS

RELATED APPLICATION

This is a continuation-in-part of application Ser. No. 049,390 filed June 18, 1979, now abandoned.

The present invention relates to α-prop-1-ynyl-3-phenoxybenzyl alcohols, a process for their manufacture and their use as intermediates for the synthesis of compounds which are suitable for pest control.

The α-prop-1-ynyl-3-phenoxybenzyl alcohols have the formula

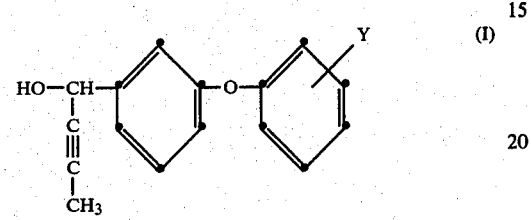

wherein Y represents hydrogen, halogen, $C_1$-$C_4$ alkyl, $C_1$-$C_3$alkoxy, cyano or dimethylamino.

Halogen denotes fluorine, chlorine, bromine or iodine, but is in particular fluorine, chlorine or bromine.

The alkyl and alkoxy groups are methyl, methoxy, ethyl, ethoxy, propyl, propoxy, isopropyl, isopropoxy, n-butyl, isobutyl, sec- and tert-butyl.

Particularly suitable intermediates are compounds of the formula I, wherein Y represents hydrogen, fluorine, chlorine, bromine, methyl or methoxy.

The compounds of the formula I can be obtained by methods analogous to known ones, for example as follows:

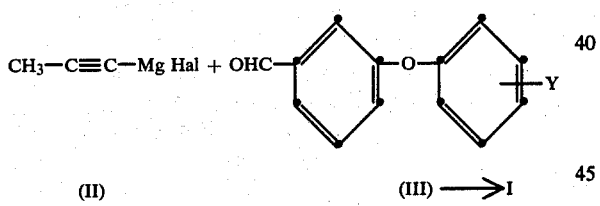

In formula III, Y is as defined for formula I and in formula II, Hal represents a halogen atom, especially chlorine or bromine.

The process is carried out at a reaction temperature in the range between −10° C. and 100° C., preferably between 0° C. and 80° C., usually under normal pressure and in an inert solvent or diluent. Suitable solvents or diluents are, in particular, ethers, such as diethyl ether, tetrahydrofurane and dioxane. The starting materials of the formulae II and III are known or they can be prepared by methods analogous to known ones.

The compounds of the formula I are suitable in particular as intermediates for the manufacture of compounds (cf. Example 1 b) which are suitable for controlling pests, in particular insects and representatives of the order Acarina and which are better suitable because of their low fish toxicity, for the control of rice pests, e.g., *Chilo suppressalis* in rice paddies where fish are kept, than compounds known from the Great Britain Pat. No. 1,438,129 and German DOS No. 2,547,554 synthesized as intermediates with the alcohols of the formulae

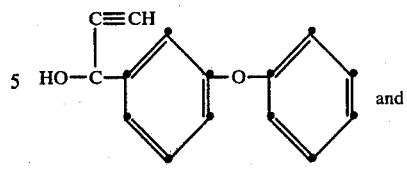

and

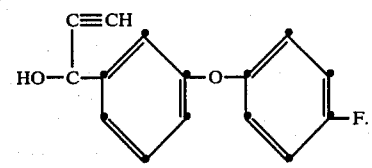

EXAMPLE 1

(a) Manufacture of α-prop-1-ynyl-3-phenoxybenzyl alcohol

A Grignard solution freshly prepared from 4 g of magnesium and 20 g of ethyl bromide in 20 ml of tetrahydrofurane is slowly added at 0° C. to a solution of 8 g of methyl acetylene in 100 ml of tetrahydrofurane, and the mixture is stirred under argon for 15 minutes. A solution of 27 g of 3-phenoxybenzaldehyde in 100 ml of tetrahydrofurane is then added dropwise to the above mixture.

After stirring for 14 hours at room temperature, the reaction mixture is cooled to 0° C. with ice and, after the slow addition of 25 ml of conc. hydrochloric acid, extracted with ether. The ethereal extract is washed twice with water and twice with saturated sodium chloride solution, dried over sodium sulfate, filtered and concentrated. The product is chromatographed over silica gel with ethyl acetate/hexane (1:4) as eluant, affording the compound of the formula

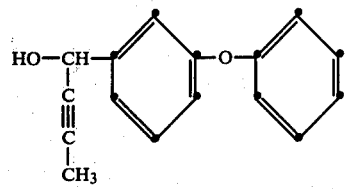

with a refractive index of $n_D^{20°} = 1.5898$.

The following compounds are also prepared in analogous manner:

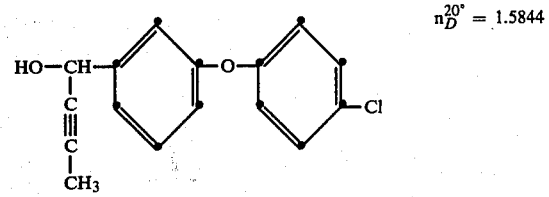

$n_D^{20°} = 1.5844$

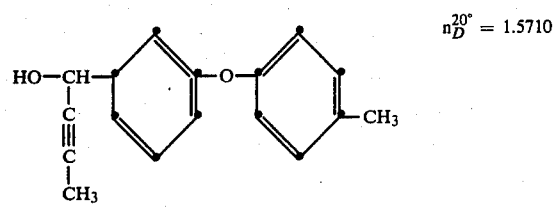

$n_D^{20°} = 1.5710$

-continued

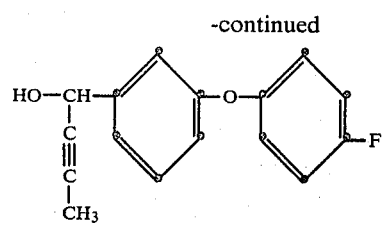

$n_D^{20°} = 1.5669$

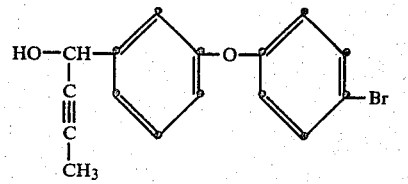

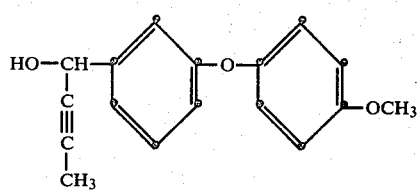

(b) Manufacture of
α-prop-1-ynyl-3-phenoxybenzyl-2,2-dimethyl-3-(2',2'-dichlorovinyl)cyclopropane-1-carboxylate A solution of 4 g of α-prop-1-ynyl-3-phenoxybenzyl alcohol in 20 ml of toluene is added dropwise to an ice-cooled solution of 3.82 g of 2,2-dimethyl-3-(2',2'-dichlorovinyl)cyclopropanecarboxylic acid chloride and 1.8 ml of pyridine in 50 ml of toluene. The reaction mixture is stirred for 14 hours at room temperature and then extracted with ether. The ethereal extract is washed once with water, once with 2 N hydrochloric acid and three times with saturated sodium chloride solution, then dried over sodium sulfate, filtered and concentrated. The product is chromatographed over silica gel with ether/hexane (1:3) as eluant, affording the compound of the formula

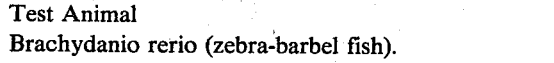

as a diastereoisomer mixture with a refractive index of $n_D^{20°} = 1.5700$.

EXAMPLE 2

Comparison test

Test compounds

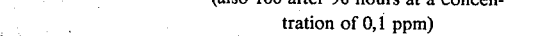

A

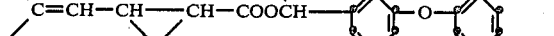

B

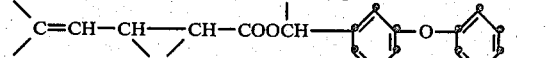

C

U.S. Pat. Application Serial No. 216,222

D

Great Britain Patent No. 1,438,129 - Example 2

E

DOS 2,547,534 - Compound No. 8

Test Animal
Brachydanio rerio (zebra-barbel fish).
Test
4 Zebra barbel fishes of 2 cm length (Brachydanio rerio) were put into 10 l water at a temperature of 24° C. After three days 1 mg or 10 mg of test substance, dissolved in 10 ml acetone were added.

A mortality count is made after 24, 48, 72 and 96 hours.

Test results

|  | % mortality of Brachydanio rerio by a 1 ppm aqueous solution of test compound |
|---|---|
| Compound A | 0 after 96 hours |
| Compound B | 0 after 96 hours |
| Compound C | 0 after 96 hours |
| Compound D | 100 after 24 hours |
|  | (also 100 after 96 hours at a concentration of 0,1 ppm) |
| Compound E | 100 after 96 hours |

Conclusion

Compounds A, B and C have no toxicity to the fish Brachydanio rerio at a concentration of 1 ppm whereas compounds D and E are highly toxic at the same concentration to this fish.

What is claimed is:

1. A α-prop-1-ynyl-3-phenoxybenzyl alcohol of the formula

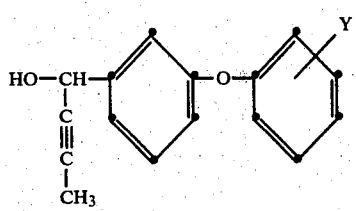

wherein Y represents hydrogen, halogen, $C_1$-$C_4$alkyl or $C_1$-$C_3$alkoxy.

2. A compound according to claim 1, wherein Y represents hydrogen, fluorine, chlorine, bromine, methoxy or methyl.

3. The compound according to claim 2 of the formula

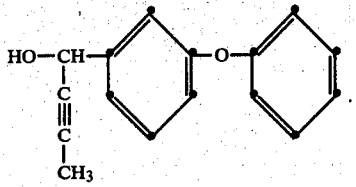

4. The compound according to claim 2 of the formula

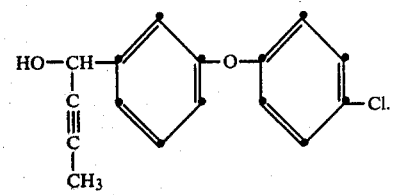

5. The compound according to claim 2 of the formula

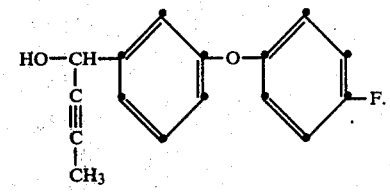

6. The compound according to claim 2 of the formula

* * * * *